United States Patent [19]
Cheng et al.

[11] Patent Number: 5,886,614
[45] Date of Patent: Mar. 23, 1999

[54] THIN FILM HYDROGEN SENSOR

[75] Inventors: Yang-Tse Cheng, Rochester Hills; Andrea A. Poli, Livonia, both of Mich.; Mark Alexander Meltser, Pittsford, N.Y.

[73] Assignee: General Motors Corporation, Detroit, Mich.

[21] Appl. No.: 837,039

[22] Filed: Apr. 11, 1997

[51] Int. Cl.[6] .................................................. H01C 7/00
[52] U.S. Cl. ................................................. 338/34; 422/90
[58] Field of Search .............................. 338/34; 73/23.2, 73/31.06, 23; 422/98, 90, 83–96

[56] References Cited

U.S. PATENT DOCUMENTS

| | | | |
|---|---|---|---|
| 4,373,375 | 2/1983 | Terhune et al. | 73/23 |
| 5,367,283 | 11/1994 | Lauf et al. | 338/34 |
| 5,373,205 | 12/1994 | Busick et al. | 327/378 |
| 5,382,943 | 1/1995 | Tanaka et al. | 340/539 |
| 5,470,756 | 11/1995 | Coles et al. | 436/144 |
| 5,561,964 | 10/1996 | McIntyre et al. | 53/75 |
| 5,670,115 | 9/1997 | Cheng et al. | 422/90 |

*Primary Examiner*—Teresa Walberg
*Assistant Examiner*—Jeffrey Pwu
*Attorney, Agent, or Firm*—Anthony Luke Simon

[57] ABSTRACT

A thin film hydrogen sensor, includes: a substantially flat ceramic substrate with first and second planar sides and a first substrate end opposite a second substrate end; a thin film temperature responsive resistor on the first planar side of the substrate proximate to the first substrate end; a thin film hydrogen responsive metal resistor on the first planar side of the substrate proximate to the fist substrate end and proximate to the temperature responsive resistor; and a heater on the second planar side of the substrate proximate to the first end.

6 Claims, 2 Drawing Sheets

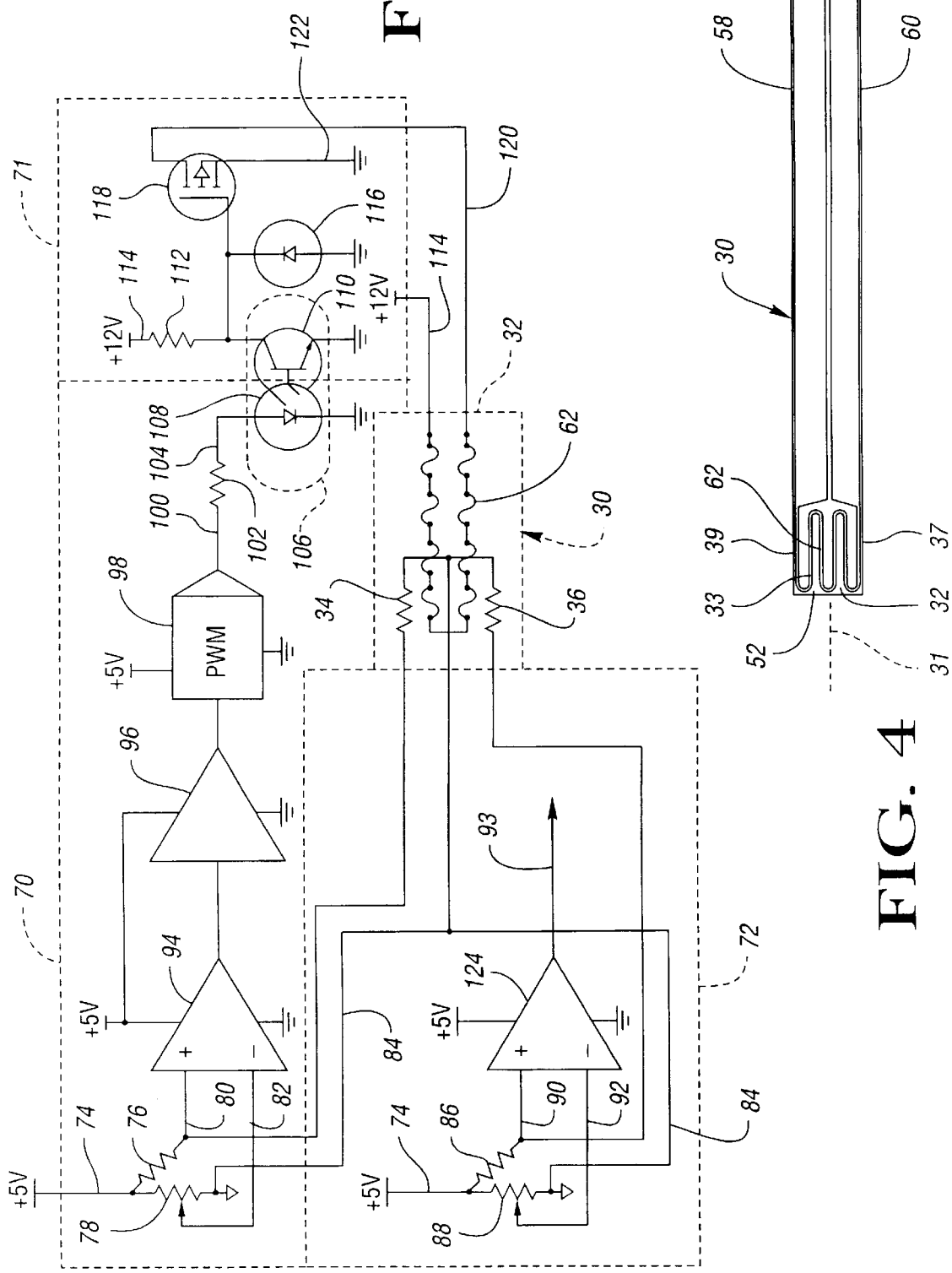

THIN FILM HYDROGEN SENSOR

The Government of the United States of America has rights in this invention pursuant to Contract No. DE-AC02-90CH10435 awarded by the U.S. Department of Energy.

This invention relates to a thin film hydrogen sensor.

BACKGROUND OF THE INVENTION

Sensing elements for some known hydrogen sensors use materials whose electrical characteristics vary in response to an amount of hydrogen gas to which the sensing element is exposed. One class of such materials includes metals that, when deposited in a thin film layer, have a resistance that varies in relation to an amount of hydrogen atoms absorbed into the metal, which depends upon the amount of hydrogen present in gases to which the thin film layer is exposed. Example metals responsive to the presence of hydrogen and suitable for use as thin film sensing elements include palladium or known palladium alloys in combination with a layer of one or more of the following: Ti, Cr, Nb, Hf, Mo, Zr, Au, Ag, Pt, Rh, Ni, and/or alloys thereof, and the like.

SUMMARY OF THE INVENTION

It is an object of this invention to provide a thin film hydrogen sensor according to claim 1.

Advantageously, this invention provides a thin film hydrogen sensor with an improved operating temperature range compared to prior known hydrogen sensors using thin film metal sensing elements.

Advantageously, this invention provides a hydrogen sensor including a thin film hydrogen responsive resistor, a thin film temperature responsive resistor and a heater, all packaged on a ceramic substrate.

Advantageously, this invention provides a hydrogen sensor with monitoring and control circuitry therefore that maintains an accurate and stable temperature control of the sensor, improving sensor precision and accuracy.

Advantageously, this invention provides a thin film hydrogen sensor in which a monitoring circuit is provided for monitoring a temperature responsive resistor and for monitoring a hydrogen responsive resistor. A control circuit is provided responsive to the monitoring circuit and electrically isolated therefrom for providing control to the sensor's heater to maintain closed loop heater control and operation of the sensor at a desired operating temperature.

Advantageously, this invention provides a thin film hydrogen sensor suitable for use in a fuel cell environment and/or a motor vehicle environment.

Advantageously, according to a preferred example, this invention provides a thin film hydrogen sensor comprising a substantially flat ceramic substrate with first and second planar sides and a first substrate end opposite a second substrate end; a thin film temperature responsive resistor on the first planar side of the substrate proximate to the first substrate end; a thin film hydrogen responsive metal resistor on the first planar side of the substrate proximate to the first substrate end and proximate to the temperature responsive resistor; and a heater on the second planar side of the substrate proximate to the first end.

In a preferred example, on the first planar side of the substrate, the temperature responsive resistor and the hydrogen responsive metal resistor are located equidistant from a center line running longitudinally through the substrate and equidistant from first and second longitudinally directed edges of the substrate. The temperature responsive resistor and the thin film hydrogen responsive metal resistor each cover substantially equal areas of the substrate and the heater on the second planar side of the substrate is symmetrical with respect to the longitudinal center line. This structure ensures that heat generated by the heater radiates equally to the temperature responsive resistor and the hydrogen responsive resistor so that the temperature responsive resistor provides an output accurately representing the temperature of the hydrogen responsive resistor.

BRIEF DESCRIPTION OF THE DRAWINGS

The present invention will now be described by way of example with reference to the following drawings in which:

FIG. 4 illustrates a second view of the example planar hydrogen sensor shown in FIG. 2; and FIG. 5 illustrates an example circuit for use with the sensor shown in FIGS. 2–4.

DETAIL DESCRIPTION OF THE INVENTION

Figure 1:
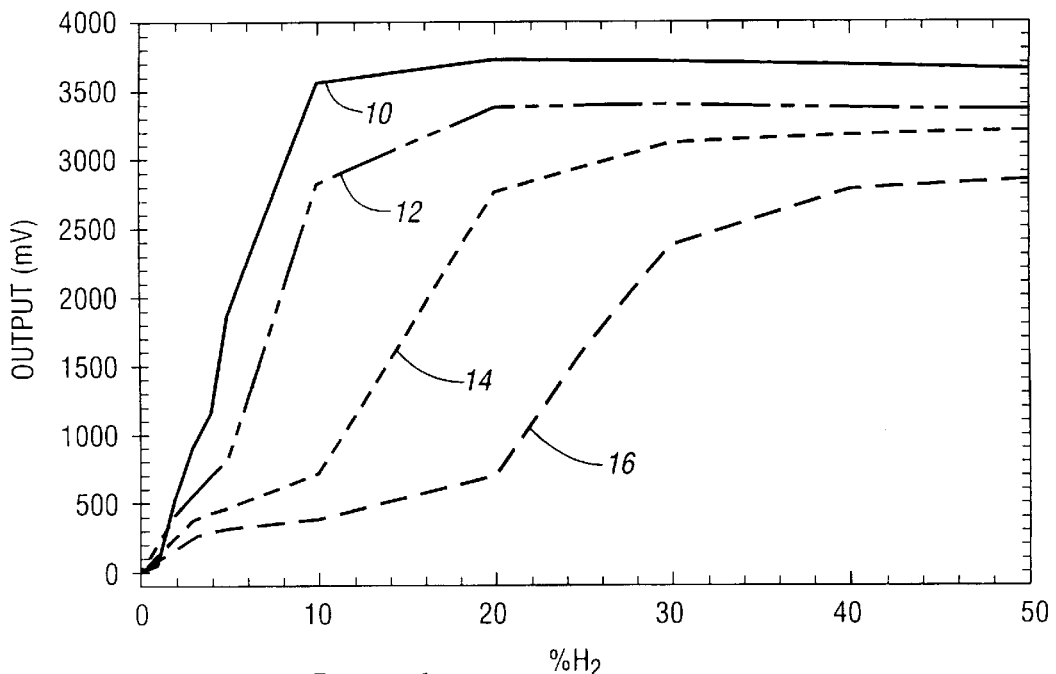
FIG. 1 illustrates an example of the temperature dependent response of a thin film metal hydrogen sensing element.

Referring now to FIG. 1, the graph shown illustrates an example response of a hydrogen sensor using a thin film metal resistor hydrogen sensing element. The graph plots the response of the sensing element to varying percentages of hydrogen for various operating temperatures of the sensor. The output signal is achieved using the thin film metal hydrogen responsive resistor connected in a four-resistor bridge with the output level of the sensor representative of the voltage output of the bridge. Traces 10, 12, 14 and 16 represent the response of the hydrogen sensing element when the sensor is maintained at 30°, 50°, 70° and 90° C., respectively, illustrating the temperature dependent nature of the response of the thin film hydrogen responsive resistor sensing element.

Another characteristic of the response of the thin film hydrogen responsive metal resistor sensing element not shown in the graph in FIG. 1 is that, as the operating temperature of the sensing element increases, the response time of the sensing element decreases. In other words, the sensor responds faster at higher operating temperatures.

Figure 2:
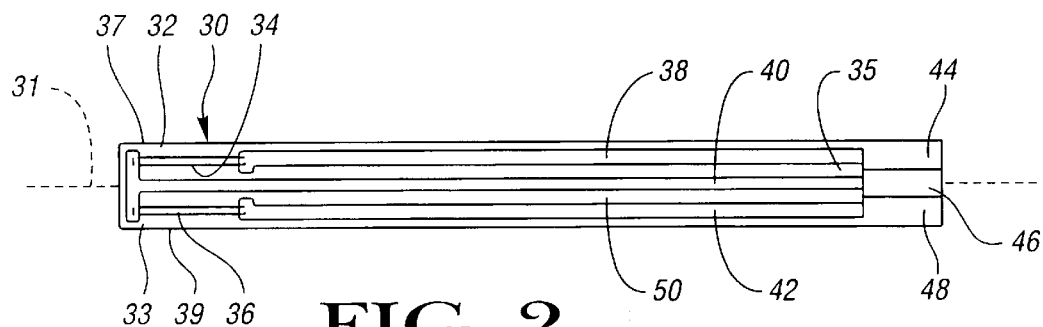
FIG. 2 illustrates a first view of an example planar hydrogen sensor according to this invention.

Referring now to FIG. 2, an example hydrogen sensor 30 according to this invention is shown. The sensor 30 includes a ceramic substrate 32 with a first planar surface 50. The preferred shape of the substrate is the elongated rectangle shown, providing first and second opposite substrate ends 33 and 35 and parallel longitudinally directed edges 37 and 39 extending between the first and second ends 33 and 35. The planar surface 50 of substrate 32 carries the temperature responsive resistor 34 (also referred to herein as sensing element 34), the hydrogen responsive resistor 36 (also referred to herein as sensing element 36), the central common conductor 40 and the separate conductors 38 and 50. The temperature responsive resistor 34 comprises a thin film of metal, such as platinum, applied to the substrate 32 by any suitable method including by electron beam deposition, ink printing or other suitable method. Similarly, the hydrogen responsive resistor 36 may also be applied to the substrate 32 by electron beam evaporation, ink printing or other suitable method. Many example suitable constructions for the hydrogen responsive metal resistor 36 are known to those skilled in the art and preferred examples include a layer of palladium deposited over a layer of platinum or a layer of palladium deposited over an alloy consisting of $Ni_{52}Zr_{48}$.

At the second end 35 of the substrate 32, platinum terminal pads 44, 46 and 48, deposited by any suitable known technique, are used for providing electrical contact between the conductors 38, 40 and 42 and electrical terminals of a known type (not shown) to which the end 35 of the substrate 32 is engaged. The non-porous substrate 32 is preferably alumina (i.e., 96% pure) and obtained by properly sintering a green body of alumina particles, binders and lubricators formed in a known manner, for example, by tape casting. The sensing element 34, 36, conductors 38, 40 and 42, and contact pads 44, 46 and 48 may be applied to the substrate after the substrate is sintered and then sintered at the desired temperature(s) or may be applied to the substrate 32 when it is a green body, before it is sintered, and then co-sintered with the substrate.

The entire surface 50, excluding the sensing elements 34 and 36 is covered with a dense alumina coating leaving the platinum pads 44, 46 and 48 exposed. The dense alumina coating may be applied by any known technique including flame spraying or by application as a separate green body layer laminated to the substrate 50 and then sintered therewith. Both the flame spraying and lamination techniques are known to those skilled in the art of flat structure ceramic technology.

Figure 3:
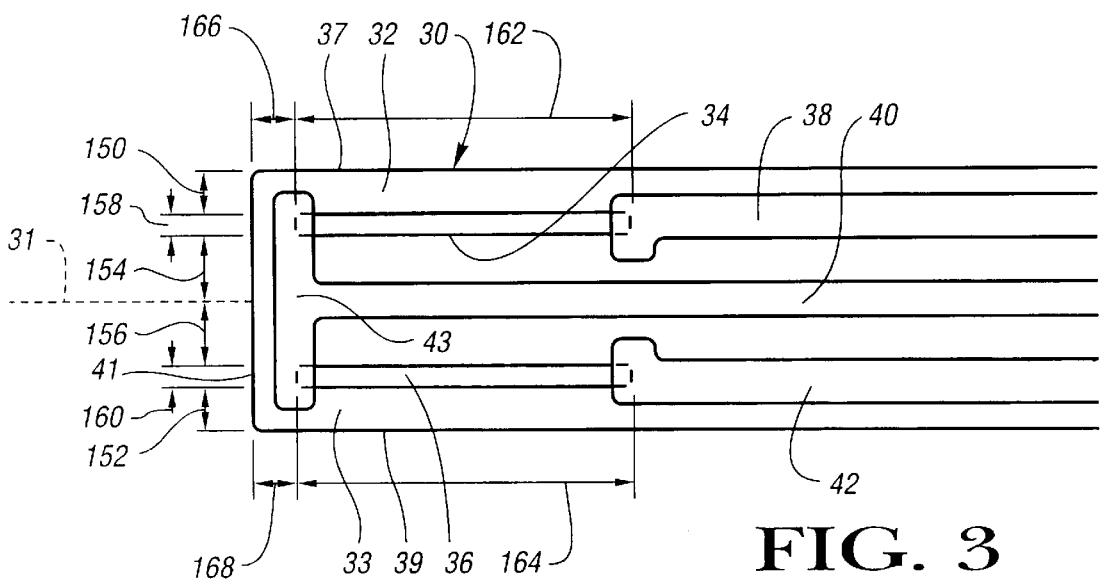
FIG. 3 illustrates an enlargement of a portion of the example sensor shown in FIG. 2.

Referring now also to FIG. 3, the entire structure of the first planar side of the sensing element 32, particularly on the end 33 of the substrate 32, is symmetrical with respect to the longitudinal center line 31 of the substrate. More particularly, sensing elements 34 and 36 are located substantially equal distances 154 and 156 from the longitudinal center line 31. Further, sensing element 34 has a width 158 and length 162 substantially equal to the width 160 and length 164 of the sensing element 36 so that both sensing elements 34 and 36 cover substantially equal surface areas of the surface 50 of the substrate 32. The sensing elements 34 and 36 are at equal distances 150 and 152 from the edges 37 and 39 of the substrate 32 and at equal distances 166 and 168 from the edge 41 of the substrate 32. Both sensing elements 34 and 36 are identically aligned, parallel with the longitudinal center line 31. It is also seen that the structure of the conductors 38, 40 and 42 is symmetrical with respect to the longitudinal center line 31. Conductor 40, having a symmetrical T-shape is centered on the center line 31 and conductors 38 and 42 are diametrically opposed on opposite sides of center line 31.

Referring now also to FIG. 4, on the second planar surface 52 of the substrate 32, a serpentine heating element 62, for example of thin or thick film platinum, is coupled to conductors 58 and 60 whose ends 54 and 56 at the end 35 of the substrate serve as the contact terminals for providing electrical connection to a connector of a known type. The conductors 58 and 60 are made substantially wider than the conductors 38, 40 and 42 (FIG. 2) to allow the conductors 58 and 60 to carry the amount of current necessary to operate the heater 62 at the desired temperature (i.e., 300° C. or higher).

Heater 62 and conductors 58 and 60 are also symmetrical with respect to the longitudinal center line 31 of the sensor 30. This structure ensures equal heating to both longitudinal halves of the sensor 30 on each side of the longitudinal center line 31.

Additionally, the symmetrical structure on the first planar surface 50 shown in FIGS. 2 and 3 provides for equal heat transfer profiles of the sensor 30 on each side of the center line 31. The sensing elements 34 and 36 receive equal heat profiles with respect to the longitudinal center line 31 because they, along with the heater 62, are positioned and shaped symmetrically with respect to the longitudinal center line 31. Thus the temperature to which the temperature responsive resistor comprising sensing element 34 is exposed is equal to the temperature to which the hydrogen responsive resistor comprising sensing element 36 is exposed. This structure ensures that the temperature sensed by sensing element 34 represents the temperature of sensing element 36 in both thermally static and thermally dynamic conditions.

The conductor 40 is connected through its T-shaped end 43 to a first end of sensing element 34 and a first end of sensing element 36. The conductor 38 is connected to the second end of sensing element 34 and the conductor 42 is connected to the second end of sensing element 36.

Referring now to FIG. 5, the example circuitry comprises power circuit 71 for providing power to the heater 62 and monitoring circuits 70 and 72 for monitoring the output of the sensing elements 34 and 36. The monitored circuit 72 includes a resistor bridge comprising resistor 86 in series with hydrogen responsive resistor 36 connected between a regulated voltage supply line 47 and circuit ground 84 and a pair of resistances represented by the portions of resistor 88 on each side of the center tap 92. Resistor 88 is also coupled between the regulated voltage supply line and ground.

With resistor 86 fixed and both resistances 88 fixed, the output of the bridge on lines 90, 92 varies with the resistance of sensing element 36, which varies with the amount of hydrogen in the atmosphere to which sensing element 36 is exposed. The signals on lines 90 and 92 are input to differential amplifier 124, which provides an output signal on line 93 indicative of the hydrogen content of the atmosphere to which the end 33 of sensor 30 is exposed.

The monitoring circuit for the temperature responsive resistor comprising sensing element 34 also includes a resistor bridge with resistor 76 and sensing element 34 connected in series and the two resistances of resistor 78 on either side of center tap 82 coupled parallel to resistor 76 and sensing element 34 between the fixed voltage supply line 74 and ground 84. Because the resistor 76 is fixed and the two resistances of resistor 78 on either side of center tap 84 are fixed, the output of the bridge on lines 80 and 82 is responsive to the resistance of sensing element 34, which varies with the temperature of the end 33 of substrate 32.

The signals across lines 80 and 82 are input to amplifier 94 that provides an output responsive to the difference in voltage levels on lines 80 and 82. The output of amplifier 94 is connected to amplifier 96 to further amplify the signal and provide that further amplified signal to the input of PWM circuit 98. PWM circuit 98 is a circuit of a known type that provides a pulse width modulated signal at its output line 100 responsive to the voltage at the input. The output of PWM circuit 98 on line 100 is a pulse width modulated signal responsive to the temperature of the end 33 of substrate 32 as sensed by sensing element 34 and is coupled via resistor 102 and line 104 to the light source 108 of optical coupler 106.

Optical coupler 106 is a device of a known type for transferring a control signal such as the PWM signal on line 104, from a control circuit having one power supply, for example the regulated five volt power supply line 74, to a power source having a separate power supply, for example, the 12 volt power supply line 114. The optical coupler 106 includes a solid state switching device, such as transistor 110, that is responsive to the optical output of light source 108, turning on and off as light source 108 is switched on and off. The transistor 110 is coupled to the 12 volt supply line 114 via resistor 112 and is also coupled to the gate input of power FET 118 with a diode 116 provided for reverse voltage protection.

The pulse width modulation of light source 108 via the signal on line 104 in turn pulse width modulates the transistor 110, which pulse width modulates the control gate of FET 118. FET 118 pulse width modulates the power supplied to heater 62, which is coupled between the 12 volt supply line 114 and line 120, which power FET 118 selectively couples to ground 122

This arrangement provides continuous feedback of the control of the heater 62 via the temperature of the end 33 of the substrate 32 as sensed by sensing element 34. The target temperature to which the heater 62 is controlled is set by the position of center tap 82 in resistor 78 (obviously, resistor 78 can be replaced by two discrete resistors).

Through the circuit structure shown, the sensing elements 34 and 36 on the surface 50 of the substrate 32 are connected only to circuitry coupled to the regulated power supply line 74 and are electrically isolated from the power supply line 114 and the power supply circuitry 71 for the heater 62. This is true even though the power to the heater 62 from the power supply circuitry 71 is controlled by the monitoring circuit 70.

The advantage of the pulse width modulated control for the heater shown is that temperature is controlled continuously through variations of the duty cycle of the pulse width modulated control signal output from the monitoring circuit 70. That is, the pulse width modulated control signal is continuously applied unless the temperature of the end 33 of the substrate 32 is greater than the temperature set by line 82 via the center tap on resistor 78. When the temperature sensed by sensing element 34 is below the target temperature set by line 82, the duty cycle on line 104 increases the further the temperature sensed by sensing element 34 is from the target temperature set by line 82. This continuous heater control eliminates fluctuations that may result in heaters that are discretely switched on and switched off in response to sensed temperature.

Additionally, the switched mode of power delivery provided by the PWM control is suitable for environments such as in fuel cell stacks or such as in fuel cells included in automotive vehicles in which the high powered supply line, i.e., the 12 volt supply line 114, is subject to variation with vehicle or other load running conditions.

We claim:

1. A thin film hydrogen sensor comprising:
   a substantially flat ceramic substrate with first and second planar sides and a first substrate end opposite a second substrate end;
   a thin film temperature responsive resistor on the first planar side of the substrate proximate to the first substrate end;
   a thin film hydrogen responsive metal resistor on the first planar side of the substrate proximate to the first substrate end and proximate to the temperature responsive resistor; and
   a heater on the second planar side of the substrate proximate to the first substrate and, also comprising
      a monitoring circuit coupled to the temperature responsive resistor and to the hydrogen responsive metal resistor; and
   a power circuit coupled to the healer, wherein the power supply circuit is electrically isolated from the monitoring circuit and is responsive to the monitoring circuit for providing power to the heater, wherein the heater maintains the first substrate end at a control temperature higher than a highest desired operating temperature of the thin film hydrogen sensor.

2. A thin film hydrogen sensor comprising:
   a substantially flat ceramic substrate with first and second planar sides and a first substrate end opposite a second substrate end;
   a thin film temperature responsive resistor on the first planar side of the substrate proximate to the first substrate end;
   a thin film hydrogen responsive metal resistor on the first planar side of the substrate proximate to the first substrate end and proximate to the temperature responsive resistor;
   a heater on the second planar side of the substrate proximate to the first substrate end;
   a first conductor, connecting a first end of the temperature responsive resistor and a first end of the hydrogen responsive metal resistor and extending along the first planar side from the first substrate end to the second substrate end;
   a second conductor connecting to a second end of the temperature responsive resistor and extending along the first planar side from the first substrate end to the second substrate end; and
   a third conductor connecting to a second end of the hydrogen responsive metal resistor and extending along the first planar side from the first substrate end to the second substrate end, also comprising
      a monitoring circuit coupled to the temperature responsive resistor and to the hydrogen responsive metal resistor, wherein the monitoring circuit comprises:
         a first resistor bridge circuit comprising the temperature responsive resistor and first, second and third bridge resistors wherein the first resistor bridge circuit is coupled to the first and second conductors;
         a second resistor bridge circuit comprising the hydrogen responsive resistor and fourth, fifth and sixth bridge resistors, wherein the second resistor bridge circuit is coupled to the first and third conductors.

3. A thin film hydrogen sensor according to claim 2, also comprising:
   a first differential amplifier within the monitoring circuit, responsive to the first resistor bridge circuit and providing an output signal indicative of a temperature of the first substrate end;
   a pulse width modulation control circuit within the monitoring circuit, responsive to the output of the first differential amplifier providing a pulse width modulated signal output;
   a signal coupler including a light source and an optically controlled solid state switch, wherein the light source is coupled to the pulse width modulated signal output; and
   a power circuit coupled to the solid state switch, providing a pulse width modulated power signal to the heater responsive to the light source, wherein the power circuit and monitoring circuit remain electrically isolated.

4. A thin film hydrogen sensor according to claim 3, also comprising:
a second differential amplifier within the monitoring circuit, wherein the second differential amplifier is responsive to the second resistor bridge circuit and provides an output signal indicative of an amount of hydrogen to which the first end of the substrate is exposed.

5. A thin film hydrogen sensor comprising:
a substantially flat ceramic substrate with first and second planar sides and a first substrate end opposite a second substrate end;
a thin film temperature responsive resistor on the first planar side of the substrate proximate to the first substrate end;
a thin film hydrogen responsive metal resistor on the first planar side of the substrate proximate to the first substrate end and proximate to the temperature responsive resistor; and
a heater on the second planar side of the substrate proximate to the first substrate end, also comprising
a first conductor, connecting a first end of the temperature responsive resistor and a first end of the hydrogen responsive metal resistor and extending along the first planar side from the first substrate end to the second substrate end, wherein the first conductor is longitudinally centered on a center line running longitudinally through the substrate;
a second conductor connecting to a second end of the temperature responsive resistor and extending along the first planar side from the first substrate end to the second substrate end; and
a third conductor connecting to a second end of the hydrogen responsive metal resistor and extending along the first planar side from the first substrate end to the second substrate end, wherein the second and third conductors are diametrically opposed with respect to the longitudinal center line.

6. A thin film hydrogen sensor according to claim 5, wherein the first conductor includes a conductor end extending laterally in first and second directions to form a T-shape symmetrical with the center line, wherein the conductor end forms the connections to the temperature responsive resistor and to the hydrogen responsive metal resistor.

* * * * *